__United States Patent__ [19]

Pugach et al.

[11] Patent Number: 4,945,184

[45] Date of Patent: Jul. 31, 1990

[54] PREPARATION OF UNSATURATED KETONES

[75] Inventors: Joseph Pugach, McCandless Township, Allegheny County; Jeffrey S. Salek, Oakdale Borough, Allegheny County, both of Pa.

[73] Assignee: Aristech Chemical Corporation, Pittsburgh, Pa.

[21] Appl. No.: 367,902

[22] Filed: Jun. 19, 1989

[51] Int. Cl.$^5$ ................................................ C07C 45/75
[52] U.S. Cl. .................................... 568/313; 568/345; 568/390
[58] Field of Search .............. 568/388, 390, 345, 353, 568/313, 312

[56] References Cited

U.S. PATENT DOCUMENTS

| | | | |
|---|---|---|---|
| 2,064,564 | 12/1936 | Quattlebaum, Jr. | 260/134 |
| 2,309,727 | 2/1943 | Barnes | 260/66 |
| 2,462,031 | 2/1949 | Wittcoff | 568/345 |
| 3,322,832 | 5/1967 | Cragoe | 568/313 |
| 3,928,457 | 12/1975 | Ember | 568/390 |
| 4,010,204 | 3/1977 | Köster et al. | 260/586 C |
| 4,035,395 | 7/1977 | Stetter et al. | 260/347.5 |
| 4,146,581 | 3/1979 | Nissen et al. | 568/313 |
| 4,355,184 | 10/1982 | Kaku et al. | 568/388 |

FOREIGN PATENT DOCUMENTS 506850 6/1939 United Kingdom ................ 568/390

OTHER PUBLICATIONS

Hays et al, "Condensation of Formaldehyde with Compounds Containing Activated Hydrogens", *J. Am. Chem. Soc.*, vol. 73, pp. 5369-5373 (Nov. 1951).

*Primary Examiner*—James H. Reamer
*Attorney, Agent, or Firm*—William L. Krayer

[57] ABSTRACT

Unsaturated ketones are produced from ketones and paraformaldehyde under mild reaction conditions utilizing a catalyst comprising a halogen acid salt of a secondary amine and a small amount of a carboxylic acid. Temperatures of 120°–150° C. and pressures of 775–1135 kilopascals are preferred. Di-unsaturated ketones such as divinyl ketone may also be produced; if the starting ketone already has an unsaturated group, a second unsaturated group will be produced.

15 Claims, No Drawings

PREPARATION OF UNSATURATED KETONES

TECHNICAL FIELD

This invention relates to the conversion of ketones, especially acetone, to unsaturated ketones and particularly to conjugated unsaturated ketones. Typical is the reaction of acetone with paraformaldehyde at temperatures of about 120°–150° C. and pressures of 780–1135 kilopascals in the presence of a catalyst comprising a halogen acid salt of a secondary amine and a small amount of a carboxylic acid to produce methyl vinyl ketone. Methyl vinyl ketone (MVK) is of current interest as a comonomer for photodegradable and biodegradable plastics and as a photosensitizer, and is of conventional use as a comonomer in various plastics and resins.

BACKGROUND OF THE INVENTION

Prior to the present invention, it has been known to react acetone with formaldehyde to obtain methyl vinyl ketone. See Embers U.S. Pat. No. 3,928,457. This patent asserts that "yields of up to 82% methyl vinyl ketone, based on formaldehyde, can be expeditiously obtained." Efficiencies with respect to acetone, however, are not as good. The '457 patent requires a catalyst of phosphoric or sulfuric acid.

A general reaction for the preparation of an alpha, beta unsaturated ketone by catalytic vapor phase condensation of formaldehyde and a ketone is disclosed in U.S. Pat. No. 3,928,458. In Table VI, the use of acetone is shown; the catalyst is a silica gel.

Alpha, beta-unsaturated ketones have been prepared by reacting ketones with formaldehyde or methanol at elevated temperatures in the presence of a heterogeneous catalyst. See equation 1. Both vapor-phase and liquid-phase processes have been used to accomplish this. See U.S. Pat. Nos. 3,578,702 and 2,451,251; British Patent No. 993,389.

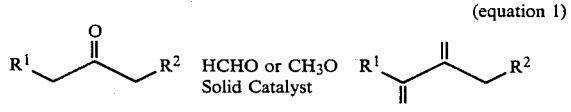

(equation 1)

However, these processes are generally uneconomical because of short-lived catalyst activity which results from the tendency of MVK and/or formaldehyde to polymerize on the surface of the catalyst. Consequently, frequent replacement or regeneration of the solid catalysts is necessary.

There are other liquid-phase processes for producing MVK discussed in the literature. One process relates to initially generating 3-keto-1-butanol from acetone and aqueous formaldehyde. See U.S. Pat. No. 3,544,634. MVK is produced by dehydration in the presence of aluminum oxide.

This particular process is limited because MVK is not formed directly and a mixture of polymethylol compounds is formed along with the desired keto-alcohol which must be separated. Another disclosure concerns generation of MVK from acetone, aqueous formaldehyde, and a strong acid (H$_2$SO$_4$, H$_3$PO$_4$, HCl, HBr, HI or p-toluenesulfonic acid). See U.S. Pat. Nos. 3,928,457 and 2,848,499. This method requires relatively harsh reaction conditions of temperature, pressure and acid dissociation constant (10$^{-4}$ or greater) while still only resulting in acetone conversions of less than 10%.

The literature also teaches the separate use of secondary amines and strong acid or weak acid salts of secondary amines for the reaction of ketones and, primarily, aldehydes, with aqueous formaldehyde (monomeric) to form the corresponding vinyl aldehyde and ketones (see Ai, M. J., *Catal.*, 1987, 106, 2734; Ueda, W. Yokoyama, T., Moro-Oka, Y., Ikawa, T., *J. Chem. Soc., Chem., Commun.*, 1984, 39.; Gutsche, D. C., Nam., K. C., *J. Am. Chem. Soc.*, 1988, 110, 6153; U.S. Pat. Nos. 4,275,242, 4,343,239, 4,406,079 and 4,496,770).

The reader may also be interested in reviewing U.S. Pat. Nos. 4,374,274, 3,928,450 and 3,701,798. The '798 patent uses an oxide of a rare earth metal as a catalyst.

SUMMARY OF THE INVENTION

Our invention achieves excellent yields and selectivities of methyl vinyl ketone (MVK) from acetone while utilizing relatively mild conditions in the liquid phase and an unexotic catalyst. We have found that certain catalyst proportions and compositions are essential for efficient results.

In a paradigm of our invention, acetone and paraformaldehyde (polymer) were reacted in the presence of a catalyst system comprising a halogen acid salt of a secondary amine and a small amount of a carboxylic acid, at 120°–150° C., at pressures of about 780–1135 kilopascals for approximately 1 hour. Typical acetone conversions approached 100 percent while MVK selectivities based on acetone were 70 to 90 percent. The reaction was very clean and the only major by-product was divinyl ketone (DVK), a desirable monomer in its own right. Acetone condensation products such as mesityl oxide and the like were not detected.

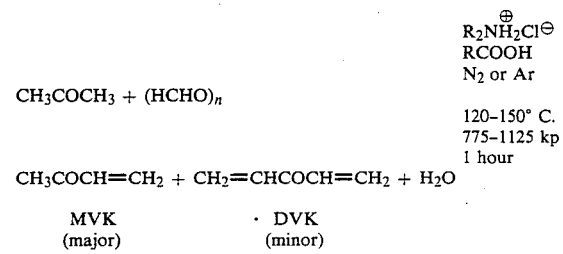

More generally, our invention is a method of making an α, β unsaturated ketone (or, in the case of an α, β unsaturated feed material, an α, β, γ, δ unsaturated ketone) comprising reacting paraformaldehyde with a ketone of the formula

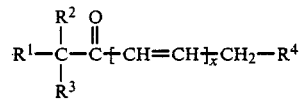

where x is 0 or 1 in the presence of an amine catalyst of the formula R$^5$R$^6$NH, a halogen acid, preferably in an amount about equimolar to the amine, and a small amount of an aliphatic or an aromatic carboxylic acid having up to about 15 carbon atoms. R$^5$ and R$^6$ may be independently selected alkyl or aryl groups having up to about 20 carbon atoms. The ratio of ketone to formaldehyde (which must be in the form of paraformaldehyde) is not critical, but is advantageously about 10:1 to about 1:10; preferably about 3:1 to about 1:3. In the higher ratios within this range, formaldehyde conversions of 95–100% are obtained with an equimolar amount of acetone (or other ketone feed) being consumed, while selectivities of vinyl ketones are 70–100%. At lower ratios, ketone conversions of 30–50% are observed with selectivities to vinyl ketones based on the starting ketone of 70–85%. Temperatures may range from about 50° C. to about 250° C., preferably 120°–150° C., and pressures from atmospheric to about 1500, preferably 775–1480 kilopascals. Use of an inert atmosphere such as argon or nitrogen is preferred but not essential. Inert solvents such as acetonitrile or 1,4-dioxane may be used if desired to dilute the reactants, but are not necessary. In batch processing, the reaction should be conducted for at least 0.25 hours, with 1–2 hours being preferred, depending on the other conditions. Reaction times beyond ten hours confer very little further advantage. A stabilizer such as hydroquinone may also be used as known in the art to prevent polymerization of the unsaturated product.

In the above general description, $R^1$, $R^2$, $R^3$ and $R^4$ may be independently chosen hydrogen, alkyl or aromatic groups having 1 to about 15 carbon atoms, including unsaturated groups provided that if both $R^1$ and $R^2$ are unsaturated, they should have a total of at least 4 carbon atoms, and also provided that $R^1$, $R^2$, $R^3$ and/or $R^4$ may form parts of the same carbon or heterocyclic ring which may have substitutions, the total number of carbon atoms thereof being up to about 30.

Examples of reactants include isophorone, acetophenone, acetone, methyl ethyl ketone, methyl vinyl ketone.

Thus, a general reaction may be depicted as:

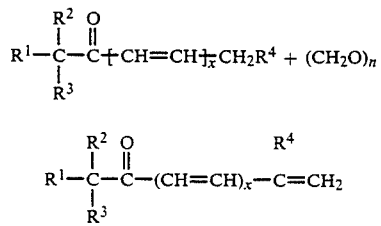

The designation $(CH_2O)_n$ denotes paraformaldehyde, which is sold as a solid having about 8 to about 100 monomer units, i.e., n is normally 8–100.

Our invention has the advantage that the presence of water is minimized, in addition to obtaining excellent yields and selectivities. One skilled in the art will recognize that paraformaldehyde is a solid and that, therefore, our process differs significantly from conventional prior art processes which utilize aqueous solutions of formaldehyde. While we have found that our results are quite distinct and surprising as compared to processes employing aqueous solutions of formaldehyde, we have observed (see Examples 37, 38, and 39 in the Table) also that the presence of as much as 30% water in the initial reaction mixture can be tolerated (although reaction efficiencies may be imparied) and, of course, the process itself generates water which does not interfere with the reaction. However, the ability to achieve a reaction mixture having a minimum of water is a significant advantage to our process.

It is understood that unsaturated groups may be placed on both sides of the carbonyl group of the ketone in the case when $R^4$ is a group $CH_2R^7$ and $R^2$ and $R^3$ are both hydrogens so that, for example,

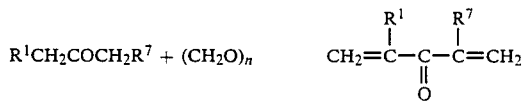

It should be noted that our process is sensitive to the presence of the carboxylic acid—that is, when we ran the reaction of acetone and paraformaldehyde (polymer) in the presence of secondary amines or their salts (with no carboxylic acid present, as in example 16 below), much poorer results were obtained than described in the literature for aqueous formaldehyde. While a very small amount of carboxylic acid will have at least some beneficial effect in our process, we have found that about 0.01 equivalent of carboxylic acid per equivalent of ketone is an optimum; use of greater amounts will not produce commensurately more beneficial results. At least about 0.005 equivalent COOH is preferred. Furthermore, it was surprising and unexpected how well paraformaldehyde worked (only in the presence of our catalyst) since it is known that paraformaldehyde decomposes to the monomer (the normally reactive species) only in the presence of strong acids and at temperatures approximating 170° C. (see Bevington, T., Q. Rev., Chem. Soc., 1952, 6, 141.; U.S. Pat. Nos. 4,340,767; 3,925,488 and 3,026,264; Japan Patent No. 59 55,849; Process Economics Program (Formaldehyde; Report No. 23), Stanford Research Institute, Menlo Park, California, 1967, pp. 45–46, 154. 1, 3, 5-Trioxane (the cyclic trimer of formaldehyde) also gave poor results with our catalyst system, again demonstrating the uniqueness of the paraformaldehyde/catalyst combination.

The catalyst may comprise a reaction product, i.e. a combination of a secondary amine and an acid salt such as hydrochloric acid. Examples of suitable amines are piperidine, dibutyl amine, piperazine, dioctyl amine, diethyl amine, dipropyl amine, pentyl n-butyl amine, diisobutylamine, dihexyl amine and the halogen acid salts thereof. Examples of suitable carboxylic acids are acetic, propionic, succinic, benzoic, malic, stearic acid and the like. The molar ratio of amine acid salt to the carboxylic acid may be about 0.5:1 to about 10:1, preferably about 2.5:1.

The amine catalyst should be present in an amount representing from about 0.01 to about 0.1 equivalent per equivalent of the starting ketone feed.

DETAILED DESCRIPTION OF THE INVENTION

In the Table, the results are shown for various experiments including some conducted according to one of the three following general procedures.

The general procedure used for the vinylation of acetone with an initial 3:1 ratio of acetone to formaldehyde equivalent was:

A reaction mixture containing acetone (3.0 equiv.), paraformaldehyde (formally 1.0 equiv.), hydroquinone (0.0015 equiv.), secondary amine halogen acid salt (e.g., piperidine hydrochloride; 0.075 equiv.) and organic carboxylic acid (e.g., propionic acid; 0.030 equiv.) was charged into a Parr autoclave under an inert atmosphere (e.g., argon or nitrogen). The autoclave was pressurized with the inert gas (435–785 kp) and the charge was rapidly heated and maintained at 120°-150° C. (775-1800 kp). After a reaction time of 1-2 hours, the charge was rapidly cooled in an ice-water bath. G.C. analysis commonly revealed acetone conversions of 32-36% (95-100% based on reacted formaldehyde), formaldehyde conversions approximating 100% and MVK and DVK selectivities based on reacted acetone of 70-90% and 2-5%, respectively. Isolation of acetone and MVK, each at greater than 99% purity, was accomplished by atmospheric fractional distillation.

The general procedure used for vinylation of acetone (initially equimolar ratio of acetone to formaldehyde equivalent) was:

A reaction mixture containing acetone (1.0 equiv.), paraformaldehyde (formally 1.0 equiv.), hydroquinone (0.0005 equiv.), secondary amine halogen acid salt (e.g., piperidine hydrochloride; 0.025 equiv.) and organic carboxylic acid (e.g., propionic acid; 0.010 equiv.) was charged into a Parr autoclave under an inert atmosphere (e.g., argon or nitrogen). The autoclave was pressurized with the same gas (780-1135 kp) and the charge was rapidly heated and maintained at 120°-150° C. (780-1800 kp). After a reaction time of 1-2 hours, the charge was rapidly cooled by submerging the reaction chamber in an ice-water bath. G.C. analyses commonly revealed acetone conversions of 30-50% and MVK and DVK selectivities based on reacted acetone of 70-85% and 2-5%, respectively. Unreacted solid paraformaldehyde was observed at the conclusion of the reaction. Atmospheric fractional distillation recovered both acetone and MVK each at greater than 99% purity.

The general procedure for the vinylation of acetophenone employed a reaction mixture containing acetophenone (1.0 equiv.; hydrochloride; 0.025 equiv.) and organic carboxylic acid (e.g., propionic acid; 0.010 equiv.). The procedure was as otherwise described above, acetophenone conversions (3:1 acetophenone to formaldehyde equivalent) of 80-90% and phenyl vinyl ketone (PVK) selectivities of 80-90% were observed.

As will be seen from the table to follow, it is essential to our process that paraformaldehyde be used as the formaldehyde reactant rather than an aqueous form such as commonly used in the past and/or rather than 1, 3, 5-trioxane.

In the following table, each example represents a separate experiment. Examples 1-41 all employed an acetone feed. Thereafter, the initial feed was as indicated in the table.

Paraformaldehyde was employed in all cases except example 1, which used a 37% aqueous solution of formaldehyde, and 11, which employed 1, 3, 5-trioxane, each in an amount equimolar to the starting ketone feed material. The carboxylic acid catalyst was propionic acid in all cases but 7, which was malic acid, 14 (none), 15 (n-butyric), 19 (benzoic) and 28 ($CH_3COOH$), each in the amount of 0.010 equivalent. The amine catalyst was varied as shown in the table. All examples employed hydroquinone as a stabilizer and dioxane as a solvent or G.C. internal standard except 20 (acetonitrile instead of dioxane), 21 (hydroquinone only), and 45 (hydroquinone only).

| | Products | | Amine Catalyst | Time (h) | Temp (°C.) | Press. (Kilo- pascals) | % Conv.* | % Sel. | COMMENTS: |
|---|---|---|---|---|---|---|---|---|---|
| 1. | O= (Major) | (Minor) | NH.HCl (cyclohexyl) | 1.1 | 90-120 | 370-445 | 16-20 | 15-25 (MVK) <0.1 (DVK) | Comparison example: 37% aqueous formaldehyde. |
| 2. | O= (Major) | (Minor) | NH.HCl | 0.5-1.0 | 90-150 | 370-510 | 30-35 | 65-80 (MVK) 1-5 (DVK) | Paraformaldehyde; shorter reaction time. |
| 3. | O= (Major) | (Minor) | NH.HCl | 1.0-2.0 | 90-150 | 370-510 | 30-40 | 65-80 (MVK) 1-5 (DVK) | Paraformaldehyde; longer time. |
| 4. | O= (Major) | (Minor) | NH.HCl | 0.5-1.0 | 120-150 | 775-1125 | 30-40 | 70-85 (MVK) 1-5 (DVK) | Paraformaldehyde, higher pressure. |
| 5. | O= (Major) | (Minor) | NH.HCl | 1.0-2.0 | 120-150 | 780-1125 | 30-40 | 70-85 (MVK) 1-5 (DVK) | Repeat 4 with longer time and higher pressure. |
| 6. | O= (Major) | (Minor) | NH | 1.2 | 110-130 | 985-1055 | 53 | 6.5 (MVK) <1 (DVK) | Neutral piperidine catalyst; low selectivity. |

-continued

| | Products | | Amine Catalyst | Time (h) | Temp (°C) | Press. (Kilopascals) | % Conv.* | % Sel. | COMMENTS: |
|---|---|---|---|---|---|---|---|---|---|
| | (Major) | (Minor) | | | | | | | |
| 7. | 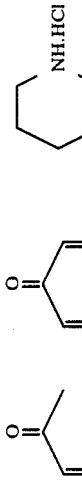 | 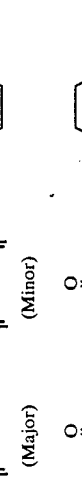 | cyclohexyl-NH·HCl | 1.2 | 140–170 | 915–990 | 36–38 | 59–63 (MVK) 2 (DVK) | Malic acid was used instead of propionic. |
| 8. | 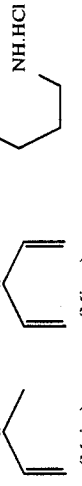 | 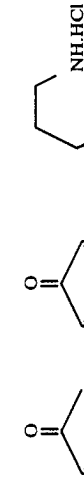 | cyclohexyl-NH·HCl | 6.75 | 120–140 | 915–1090 | 45 | 23 (MVK) <1 (DVK) | Much longer reaction time. Selectivity drops. |
| 9. | 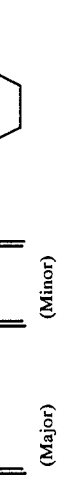 | 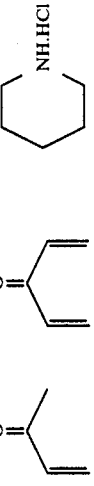 | cyclohexyl-NH·HCl | 0.25 | 50–60 | 440–580 | 2 | 60 (MVK) 2 (DVK) | Short reaction time. Conversion drops. |
| 10. | 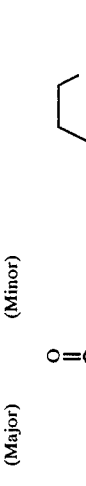 | 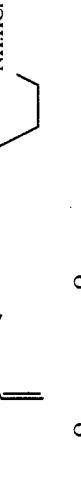 | cyclohexyl-NH·HCl | 0.25 | 120–140 | 915–990 | 4 | 61 (MVK) 2 (DVK) | High temperature and pressure; short reaction time. Low conversion. |
| 11. | 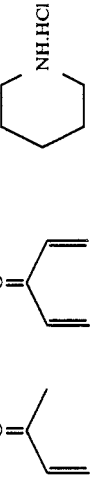 | | cyclohexyl-NH·HCl | 1.1 | 110–140 | 850–920 | 4 | 0.8 | 1, 3, 5 trioxane instead of paraformaldehyde. Small conversion; very low selectivity. |
| 12. |  |  | cyclohexyl-NH·HCl | 1.0 | 120–130 | 915–1055 | 55 | 35 (MVK) 1 (DVK) | Increased amine catalyst 4-fold. |
| 13. |  |  | None | 1.1 | 120–140 | 915–1055 | 24 | 7 | No amine catalyst. |

-continued

| | Products | | Amine Catalyst | Time (h) | Temp (°C.) | Press. (Kilo-pascals) | % Conv.* | % Sel. | | COMMENTS: |
|---|---|---|---|---|---|---|---|---|---|---|
| 14. | (Major) | (Minor) | cyclohexyl-NH·HCl | 1.1 | 110–120 | 915–1055 | 53 | 27 (MVK) | 1 (DVK) | No carboxylic acid catalyst. |
| 15. | (Major) | (Minor) | cyclohexyl-NH·HCl | 1.0 | 140–170 | 915–1055 | 34 | 59 (MVK) | 2 (DVK) | n-butyric acid. |
| 16. | (Major) | (Minor) | cyclohexyl-NH·HCl | 1.25 | 100–120 | 440–615 | 61–89 | 15–25 (MVK) | <1 (DVK) | Quadruple amine concentration for comparison to 12 with lower temperature and pressure. |
| 17. | (Major) | (Minor) | cyclohexyl-NH·HCl | 1.5 | 150–170 | 985–1055 | 80 | 11 (MVK) | <1 (DVK) | Excess paraformaldehyde (2:1). |
| 18. | (Major) | (Minor) | cyclohexyl-NH·HCl | 1.1 | 110–120 | 780–920 | 22 | 56 (MVK) | 1 (DVK) | Compare to 17: excess acetone (2:1 acetone:formaldehyde). |
| 19. | (Major) | (Minor) | cyclohexyl-NH·HCl | 1.0 | 120–150 | 850 | 36 | 60 (MVK) | 2 (DVK) | Benzoic acid. |

-continued

| | Products | | Amine Catalyst | Time (h) | Temp (°C.) | Press. (Kilo-pascals) | % Conv.* | % Sel. | COMMENTS: |
|---|---|---|---|---|---|---|---|---|---|
| 20. | (Major) | (Minor) | ⬡NH·HCl | 1.3 | 70–130 | 440–820 | 50 | 75 (MVK) 2–3 (DVK) | CH₃CN for internal standard. |
| 21. | (Major) | (Minor) | ⬡NH·HCl | 1.25 | 120–140 | 985–1125 | 48 | 75 (MVK) 4 (DVK) | No dioxane. |
| 22. | (Major) | (Minor) | ⬡NH·HCl | 1.1.5 | 110–150 | 140–170 | 38–45 | 60–80 (MVK) 2–4 (DVK) | 3 to 6 fold scale-up. |
| 23. | (Major) | (Minor) | (C₄H₇)₂NH·HCl | 1.25 | 120–150 | 780–1125 | 33 | 75 (MVK) 2 (DVK) | HCl salt of dibutyl amine - much better selectivity than 24. |
| 24. | (Major) | (Minor) | (C₄H₉)₂NH | 1.25 | 120–150 | 780–1125 | 39 | 13 (MVK) <1 (DVK) | Different amine catalyst - dibutyl amine. |
| 25. | (Major) | (Minor) | ⬡N—NH₂ · 2HCl | 1.2 | 130–140 | 915–990 | 32 | 51 (MVK) 3 (DVK) | Different amine. |

-continued
| | Products | | Amine Catalyst | Time (h) | Temp (°C.) | Press. (Kilo- pascals) | % Conv.* | % Sel. | COMMENTS: |
|---|---|---|---|---|---|---|---|---|---|
| 26. | 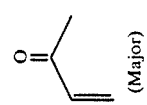 (Major) | 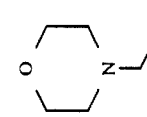 (Minor) |  H₂N · 2HCl | 1.1 | 130–140 | 915–1055 | 27 | 34 (MVK) 2 (DVK) | Different amine. |
| 27. | 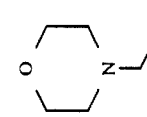 (Major) | 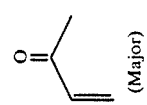 (Minor) | 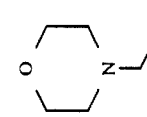 H₂N · 2HCl | 1.1 | 130–150 | 915–1055 | 35 | 36 (MVK) 3 (DVK) | Different amine. |
| 28. | 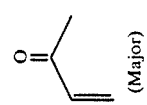 (Major) | 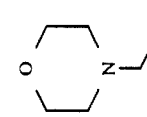 (Minor) |  H₂N · 2HCl | 1.1 | 130–140 | 915–1055 | 6 | 64 (MVK) 2 (DVK) | Different amine. |

-continued

| | Products | | Amine Catalyst | Time (h) | Temp (°C.) | Press. (Kilo-pascals) | % Conv.* | % Sel. | COMMENTS: |
|---|---|---|---|---|---|---|---|---|---|
| 29. | (Major) | (Minor) | morpholine-propyl-NH₂·HCl | 1.0 | 130–150 | 985–1125 | 23 | 53 (MVK) 2 (DVK) | Different amine. |
| 30. | (Major) | (Minor) | morpholine-ethyl-NH₂ | 1.3 | 130–150 | 985–1125 | 21 | 15 (MVK) <1 (DVK) | Different amine. |
| 31. | (Major) | (Minor) | morpholine·2HCl | 1.2 | 130–150 | 985–1125 | 23 | 52 (MVK) 2 (DVK) | Morpholine hydrochloride. |
| 32. | (Major) | (Minor) | morpholine | 1.1 | 130–150 | 985–1125 | 25 | 25 (MVK) 6 (DVK) | Morpholine without acid. Compare with 31. |
| 33. | (Major) | (Minor) | pyrrolidine·HCl | 1.1 | 130–150 | 1055–1195 | 80 | 80 (MVK) 4 (DVK) | Pyrrolidine hydrochloride. |

-continued

| | Products | | Amine Catalyst | Time (h) | Temp (°C.) | Press. (Kilopascals) | % Conv.* | % Sel. | | COMMENTS: |
|---|---|---|---|---|---|---|---|---|---|---|
| 34. | (Major) | (Minor) | Pyrrolidine NH | 1.1 | 130–150 | 985–1125 | 50 | 5 (MVK) | <1 (DVK) | Pyrrolidine with no hydrochloride: unsatisfactory selectivity. |
| 35. | (Major) | (Minor) | Piperidine·HNO₃ | 1.4 | 130–150 | 1055–1225 | 14 | 16 (MVK) | <1 (DVK) | Piperidinium nitrate. |
| 36. | (Major) | (Minor) | Piperidine·HSO₄ | 1.1 | 120–140 | 985–1125 | 38 | 7 (MVK) | <1 (DVK) | Sulfate counterion. |
| 37. | (Major) | (Minor) | Piperidine·HCl | 1.2 | 130–150 | 985–1125 | 27 | 65 (MVK) | 2 (DVK) | 5% water (by weight based on total charge). |
| 38. | (Major) | (Minor) | Piperidine·HCl | 1.1 | 130–150 | 985–1125 | 26 | 74 (MVK) | 2 (DVK) | 10% water. |
| 39. | (Major) | (Minor) | Piperidine·HCl | 1.2 | 130–150 | 985–1125 | 19 | 81 (MVK) | <1 (DVK) | 30% water. |

-continued

| | Products | Amine Catalyst | Time (h) | Temp (°C.) | Press. (Kilo-pascals) | % Conv.* | % Sel. 70-90 (MVK) 3-6 (DVK) | COMMENTS: |
|---|---|---|---|---|---|---|---|---|
| 40. |  (Major)  (Minor) |  NH.HCl | 1.1 | 130–150 | 985–1125 | 80–100 | 70-90 (MVK) 3-6 (DVK) | Acetone/formaldehyde 3:1 molar. |
| 41. |  |  NH.HCl | 1.0 | 110–140 | 435–785 | 30–40 | 80–90 | Acetophenone/formaldehyde 1:1 molar. |
| 42. |  |  NH.HCl | 1.0 | 135 | 515–785 | 20 | 80–90 | Acetephenone/formaldehyde 3:1 molar. |
| 43. |   |  NH.HCl | 1.0 | 135 | 440–785 | 30–40 | 55/35 | Isopherone/formaldehyde 1:1 molar. |
| 44. |   |  NH.HCl | 1.0 | 135 | 440–785 | 20 | 50/40 | Isopherone/formaldehyde 3:1 molar. |
| 45. |    |  NH.HCl | 1.0 | 135 | 440–785 | 50–60 | 35/35/10 | Methyl ethyl ketone/formaldehyde 1:1 molar. |

-continued

| | Products | Amine Catalyst | Time (h) | Temp (°C.) | Press. (Kilo-pascals) | % Conv.* | % Sel. | COMMENTS: |
|---|---|---|---|---|---|---|---|---|
| 46. | (dienone products) | piperidine·HCl | 1.0 | 135 | 440–785 | 20–40 | 30/30 | Mesityl oxide/formaldehyde 1:1 molar. |
| 47. | MVK / DVK | piperidine·HCl | 1.0 | 135 | 780–1465 | 40 | 74/2 | [Amino/Acid] reduced 5-fold. |
| 48. | MVK / DVK | piperidine·HCl | 1.0 | 135 | 780–1465 | 30 | 70/2 | [Amino/Acid ratio] reduced 10-fold. |
| 49. | MVK | piperazine·2HF | 1.0 | 120–150 | 775–1125 | 60 | 90 | |
| 50. | MVK | piperidine·HF | 1.0 | 120–150 | 775–1125 | 60 | 74 | |

51. An aromatic amine catalyst, diphenylamine hydrochloride (DPA.HCl), was prepared and used in the following conditions: acetone-1 equiv., paraformaldehyde-0.333 equiv., DPA.HCl-0.025 equiv., propionic acid-0.010 equiv., the reaction was conducted for 1 hour, at 140° C., about 1135–1480 kp. A 42% acetone conversion was observed while giving MVK and DVK selectivities of 90% and 3%, respectively.

52. A different hydrohalogen acid salt of piperidine was prepared (piperidine hydrobromide) and used as a catalyst as in example 51. An acetone conversion of 50% was noted with virtually quantitative selectivity to MVK and DVK (94% and 6%, respectively).

We claim:

1. Method of making a compound of the formula

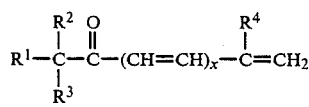

comprising reacting a ketone of the formula

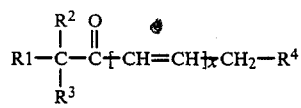

with paraformaldehyde in the presence of a catalyst comprising a secondary amine in the form of a halogen acid salt, and a small amount of a carboxylic acid having up to about 15 carbon atoms in a ratio of amine catalyst to carboxylic acid of about 0.5:1 to about 10:1, where $R^1$, $R^2$, $R^3$ and $R^4$ are independently selected from hydrogen, alkyl and aromatic groups having 1 to about 15 carbon atoms including unsaturated groups provided that if both $R^1$ and $R^2$ are unsaturated, they should have a total of at least 4 carbon atoms, and also provided that $R^1$, $R^2$, $R^3$ and $R^4$ may form parts of the same carbon or heterocyclic ring which may have substitutions the total number of carbon atoms thereof being up to about 30, and x is 0 or 1.

2. Method of claim 1 wherein the ratio of ketone to paraformaldehyde is about 10:1 about 1:10.

3. Method of claim 1 wherein the ratio of ketone to paraformaldehyde is about 3:1 to about 1:3.

4. Method of claim 1 wherein the temperature is maintained in the range of about 50° C. to about 250°.

5. Method of claim 1 wherein the pressure is maintained at about 775-1480 kilopascals.

6. Method of claim 1 wherein the amine catalyst is present in an amount from about 0.01 to about 0.1 equivalent with respect to the ketone reactant.

7. Method of claim 1 wherein the ketone feed is acetone.

8. Method of claim 1 wherein the ketone feed is isophorone.

9. Method of claim 1 wherein the ketone feed is acetophenone.

10. Method of making an unsaturated ketone comprising reacting paraformaldehyde with a ketone in the presence of a halogen acid salt of an amine catalyst of the formulas $R^5R^6NH$, where $R^5$ and $R^6$ are independently selected alkyl or aryl groups having up to about 20 carbon atoms and a carboxylic acid.

11. Method of making methyl vinyl ketone comprising reacting paraformaldehyde with acetone in the presence of a catalyst comprising a secondary amine in the form of a halogen acid salt, and a small amount of a carboxylic acid.

12. Method of making phenyl vinyl ketone comprising reacting paraformaldehyde with acetophenone in the presence of a catalyst comprising a secondary amine in the form of a halogen acid salt, and a small amount of a carboxylic acid.

13. Method of making vinyl isophorone comprising reacting paraformaldehyde with isophorone in the presence of a catalyst comprising a secondary amine in the form of a halogen acid salt, and a small amount of a carboxylic acid.

14. Method of claim 11 in which the strong acid is a halogen acid.

15. Method of claim 12 in which the strong acid is a halogen acid.

* * * * *

UNITED STATES PATENT AND TRADEMARK OFFICE
CERTIFICATE OF CORRECTION

PATENT NO. : 4,945,184

DATED : July 31, 1990

INVENTOR(S) : Joseph Pugach and Jeffrey S. Salek

It is certified that error appears in the above-identified patent and that said Letters Patent is hereby corrected as shown below:

Column 18, in the Table, Example 31, under the column entitled "Amine Catalyst", the formula

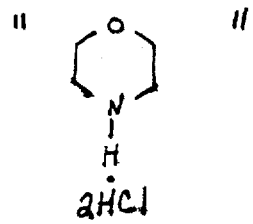

should be

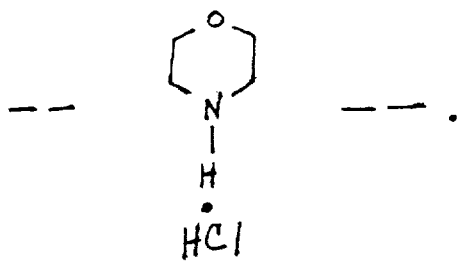

Signed and Sealed this

Twelfth Day of November, 1991

Attest:

HARRY F. MANBECK, JR.

Attesting Officer     Commissioner of Patents and Trademarks